United States Patent [19]

Papenfuhs

[11] Patent Number: 4,960,929
[45] Date of Patent: Oct. 2, 1990

[54] HYDROXYETHYLSULFONYLNITRO- AND HYDROXYETHYLSULFONYLAMINO-BENZOIC ACIDS AND PROCESSES FOR THEIR PREPARATION

[75] Inventor: Theodor Papenfuhs, Frankfurt am Main, Fed. Rep. of Germany

[73] Assignee: Hoechst Aktiengesellschaft, Frankfurt, Fed. Rep. of Germany

[21] Appl. No.: 257,741

[22] Filed: Oct. 13, 1988

[30] Foreign Application Priority Data

Oct. 17, 1987 [DE] Fed. Rep. of Germany ....... 3735268

[51] Int. Cl.$^5$ .................................... C07C 147/13
[52] U.S. Cl. ......................................... 562/430
[58] Field of Search ................................ 562/430

[56] References Cited

U.S. PATENT DOCUMENTS

| | | | |
|---|---|---|---|
| 3,250,764 | 5/1966 | Schmidt | 562/430 |
| 3,729,508 | 4/1973 | Ziegler | 562/430 |

FOREIGN PATENT DOCUMENTS

| | | |
|---|---|---|
| 938143 | 12/1955 | Fed. Rep. of Germany . |
| 3145571 | 5/1983 | Fed. Rep. of Germany . |
| 1428522 | 3/1976 | United Kingdom . |
| 2057430 | 4/1981 | United Kingdom . |

*Primary Examiner*—Michael L. Shippen

[57] ABSTRACT

A process for the preparation of compounds of the formula (5)

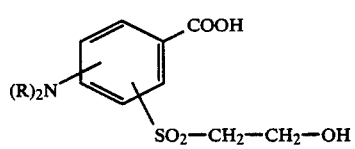

in which R denotes a hydrogen or oxygen atom and the —N(R)$_2$ group and the hydroxyethylsulfonyl group are in the ortho- or para-position relative to one another by converting 1 mol of a halonitrobenzoic acid of the formula (2)

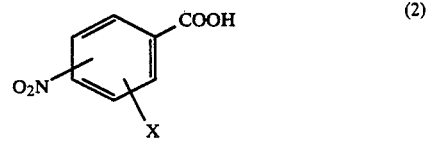

in which X denotes a fluorine, chlorine, bromine or iodine atom and the nitro group and the halogen atom are in the ortho- or para-position relative to one another, with at least 1 mol of mercaptoethanol in an aqueous solution or suspension or in an organic solvent in the presence of an acid-binding agent at temperatures from about 20° to about 100° C., to the corresponding hydroxyethylmercaptonitrobenzoic acid of the formula (3)

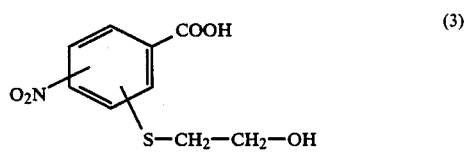

oxidizing these acids in a manner known per se to the corresponding hydroxyethylsulfonylnitrobenzoic acids of the formula (5) (R=0) mentioned and reducing the latter, if necessary, in a manner known per se to the corresponding hydroxyethylsulfonylaminobenzoic acids of the general formula (4)

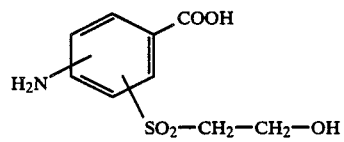

in which the amino and hydroxyethylsulfonyl group are in the ortho- or para-position relative to one another.

1 Claim, No Drawings

HYDROXYETHYLSULFONYLNITRO- AND HYDROXYETHYLSULFONYLAMINO-BENZOIC ACIDS AND PROCESSES FOR THEIR PREPARATION

The present invention relates to novel hydroxyethylsulfonylnitro- and partially novel hydroxyethylsulfonyl-amino-benzoic acids and processes for the preparation by reacting halonitrobenzoic acids with mercaptoethanol to the corresponding hydroxyethylmercaptonitrobenzoic acids, oxidizing these acids to the corresponding hydroxyethylsulfonylnitrobenzoic acids and reducing the latter, if necessary, to the corresponding hydroxyethylsulfonylaminobenzoic acids. Hydroxyethylsulfonylaminobenzoic acids are useful diazo components for the preparation of fiber-reactive azo dyes (German Patent Nos. 938,143 and 938,145), which is not only true for the hitherto known but also for the novel hydroxyethylsulfonylaminobenzoic acids, the precursors of which are the corresponding novel hydroxyethylsulfonylnitrobenzoic acids.

The hitherto known 4- and 5-hydroxyethylsulfonylanthranilic acids (German Patent No. 938,143, German Offenlegungsschriften Nos. 2,222,096, 3,145,571, 3,026,808) used for the purpose mentioned are only available by routes which are unsatisfactory in terms of engineering, ecology and economy from the sulfonic acids of the corresponding acylanthranilic acids for whose preparation likewise only industrially expensive multi-step processes are known.

Therefore, it was of great interest to provide industrially more favorable preparation processes for the abovementioned known hydroxyethylsulfonylanthranilic acids and the novel hydroxyethylsulfonylaminobenzoic acids (having a different substitution pattern). This object is achieved by the present invention.

The reason is that surprisingly it has been found that the novel hydroxyethylsulfonylnitrobenzoic acids of the general formula (1)

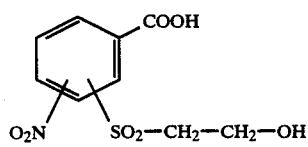
(1)

in which the nitro and hydroxyethylsulfonyl group are in the ortho- or para-position relative to one another, can be prepared in an advantageous manner by converting 1 mol of a halonitrobenzoic acid of the general formula (2)

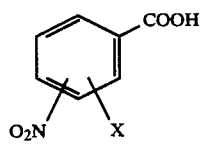
(2)

in which X denotes a fluorine, chlorine, bromine or iodine atom, preferably a chlorine or bromine atom and the nitro group and the halogen atom are in the ortho- or para-position relative to one another, with at least 1 mol, preferably 1.1 to 1.8 mol, particularly preferably 1.25 to 1.6 mol, of mercaptoethanol in an aqueous solution or suspension or in an organic solvent in the presence of an acid-binding agent at temperatures from about 20° to about 100° C., preferably about 35 to about 60° C., to the corresponding hydroxyethylmercaptonitrobenzoic acids of the general formula (3)

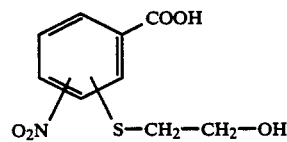
(3)

oxidizing these acids in a manner known per se to the corresponding hydroxyethylsulfonylnitrobenzoic acids of the formula (1) mentioned and reducing the latter, if necessary, in a manner known per se to the corresponding hydroxyethylsulfonylaminobenzoic acids of the general formula (4)

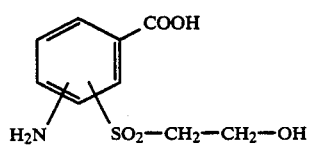
(4)

in which the amino and hydroxyethylsulfonyl group are in the ortho- or para-position relative to one another.

Starting compounds of the general formula (1) mentioned are for example: 4-chloro-3-nitrobenzoic acid, 2-chloro-5-nitrobenzoic acid, 5-chloro-2-nitrobenzoic acid, 3-chloro-4-nitrobenzoic acid, 2-chloro-3-nitrobenzoic acid and 3-chloro-2-nitrobenzoic acid.

The reaction of the compounds of the general formula (2) mentioned with mercaptoethanol is preferably carried out in an aqueous medium in the absence of an organic or other solvent. A reaction in an organic solvent can be carried out, for example, in dimethylformamide, dimethyl sulfoxide, N-methylpyrrolidone or sulfolane. If the reaction (condensation) is carried out in one of the abovementioned organic solvents, it may be necessary to dilute the reaction mixture with water before the compounds of the general formula (3) are isolated, if the isolation is desired.

The reaction of the process according to the invention is carried out in detail as follows: a halonitrobenzoic acid according to formula (2), preferably a chloro- or bromonitrobenzoic acid, is neutralized in water or one of the solvents mentioned as examples with the calculated amount of an alkali metal hydroxide or alkali metal carbonate, preferably an alkali metal carbonate, particularly preferably potassium carbonate. The mercaptoethanol is then added in the molar ratio mentioned above, and at the temperatures mentioned above and an at least equivalent amount, relative to the mercaptoethanol, of an alkali metal hydroxide or alkali metal carbonate is steadily stirred into the mixture over a period of several hours (1 to 5, preferably 2 to 4 hours). A small excess (about 5 to 30%) does not have an adverse effect on the reaction and is therefore in principle allowed, although it usually just increases the amount of salt formed without affecting the yield or purity of the desired hydroxyethylmercapto nitrobenzoic acids of the formula (3) in a significant manner. After the addition has taken place, stirring is continued at the abovementioned temperature until the condensation is completed (monitored by thin-layer or liquid chromatography), the mixture is then brought to a pH of <7.0, preferably 1 to 5, by addition of mineral acid (hydrochloric, sulfuric or phosphoric acid), as a result of which the hydroxyethylmercaptonitrobenzoic acid formed precipitates in the form of crystals and can be isolated, if necessary, by filtration or centrifugation.

As for the reaction according to the invention described (condensation) of the compounds of the general formula (2) with mercaptoethanol, it is surprising that the reaction can be carried out selectively, thus leading to high yields. Rather, it had been expected that a reductive attack on the nitro group by the mercaptoethanol in the alkaline medium of the process according to the invention would take place in preference to the desired chlorine exchange, even more so, since under the reaction conditions according to the invention the halonitrobenzoic acid substrate is not present as a possibly activating free acid but without exception as a deactivating carboxylate anion of the general formula (5)

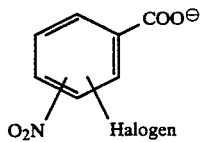
(5)

whose high water solubility, if the reaction is carried out in an aqueous medium, should also favor the competing reduction of the nitro group. In contrast, if the reaction was carried out in a solvent, it had to be expected that because of the very low solubility of the starting salts of the abovementioned formula (5) the intended exchange reaction would proceed only at a very reduced rate and thus favor side reactions.

Therefore, it was even more surprising that the desired reaction of halonitrobenzoic acids of the formula (2) mentioned with mercaptoethanol in the presence of an acid-binding agent can be carried out in the case of all substrates of the formula (2), if the reaction conditions are skilfully chosen, in such a manner that the novel hydroxyethylmercaptonitrobenzoic acids of the formula (3) are formed in high yields, then converted by oxidation of the sulfide bridge to the likewise novel hydroxyethylsulfonylnitrobenzoic acids of the formula (1), which can then be converted by reduction to partially novel, partially known hydroxyethylsulfonylaminobenzoic acids of the formula (4).

Isolation of the hydroxyethylmercaptonitrobenzoic acid is usually not required for the oxidation which follows the condensation. Rather, the oxidation can be carried out particularly advantageously directly in the condensation mixture formed, that is, in a one-pot reaction with the exchange reaction.

The detailed procedure is advantageously as follows: a mixture of isolated hydroxyethylmercaptonitrobenzoic acid and a 3- to 10-fold, preferably 4- to 6-fold, amount of water, or preferably the condensation mixture formed, is brought to a pH of <7, preferably 1 to 6, with mineral acid, and heated to temperatures of about 30 to about 90° C., preferably about 45 to about 75° C. The catalyst added is a compound of hexavalent tungsten (sodium tungstate or tungsten trioxide) in an amount of 1 to 10 parts, preferably 2 to 4 parts per mole of compound (formula (3)) to be oxidized and at least 2 mol of hydrogen peroxide (in the form of an aqueous, 20 to 85% strength, preferably 30 to 50% strength, aqueous solution) per mole of hydroxyethylmercaptonitrobenzoic acid (or in the one-pot process per mole of mercaptoethanol used) are added dropwise with stirring to the mixture over a period of 30 to 240, preferably 60 to 120, minutes (an excess of hydrogen peroxide of 5 to 30 mol %) being particularly advantageous, and the oxidation is completed by stirring for 3 to 10 hours, preferably 4 to 6 hours, at temperatures of 60° to 120° C., preferably 85° to 100° C.

This oxidation process is particularly preferred, especially for ecological reasons. However, it is also possible to use other oxidation processes known from the literature, for example using halogen in an acidic medium or hypohalite in an alkaline medium, although, as a rule, not the hydroxyethylsulfonylnitrobenzoic acids but the chloroethylsulfonylnitrobenzoic acids are formed, which, in an additional subsequent hydrolysis step, have to be converted to the former. These oxidation variations are therefore not preferred.

The hydroxyethylsulfonylnitrobenzoic acid of the formula (4), which precipitates from the oxidation mixture, if necessary after dilution with water (if a solvent-containing condensation mixture was used) upon cooling to −5° to +10° C., is isolated by filtration or centrifugation and washed with water until neutral. As a rule, drying is not necessary, since the final reduction is carried out in an aqueous medium. The reduction used can be not only one using iron (Bechamp reduction) but also, particularly advantageously, it can be a hydrogenation using catalytically activated hydrogen. The catalysts used can be not only commercially available nickel catalysts (Raney nickel or nickel supported catalysts) but also commercially available noble metal catalysts such as, for example, palladium or platinum on inert supports, preferably on activated carbons having a high specific surface area.

The reduction proceeds at elevated temperatures (about 70° to about 120° C., preferably about 80° to 100° C.) in an aqueous solution or suspension within a few hours (1 to 5 hours, preferably 1.5 to 3 hours) quantitatively and produces at the reduction temperatures mentioned aqueous solutions of the target compounds (hydroxyethylsulfonylaminobenzoic acids of the general formula (4)), from which the suspended iron oxide hydrates (in the case of Bechamp reduction) or the hydrogenating catalysts can advantageously be separated off by clarifying filtration.

From the clarified filtrate, the hydroxyethylsulfonylaminobenzoic acids of the general formula (4), if necessary after concentration by distilling off water in vacuo, can be precipitated by cooling to temperatures of −5 to +20° C. and/or salting out the product with, for example, sodium chloride or sodium sulfate and can be isolated by filtration or centrifugation.

Yields and selectivities are in all steps surprisingly high and in most cases reach values close to those expected by theory.

The examples which follow are intended to illustrate the invention in more detail, without limiting it thereto. The parts given are parts by weight.

EXAMPLE 1

105 parts of potassium carbonate are added to a mixture of 100.75 parts of 6-chloro-3-nitrobenzoic acid and 150 parts of water over a period of 20 minutes with stirring, resulting in a final temperature of about 40° C.

The mixture is heated to 75° C., and 69 parts of mercaptoethanol are then added dropwise over a period of 60 minutes, and stirring is continued for 4 hours at 90°

C. until no more starting material can be detected in the thin-layer chromatogram.

The mixture is subsequently cooled to 15° to 20° C., brought to a pH of 1 with 30% strength hydrochloric acid (about 175 parts), stirring is continued for 60 minutes at 15 to 20° C., the slightly yellow precipitate is filtered off with suction, washed free from chloride ions with cold water and dried in vacuo at 80° C.

This gives 117 parts of 2-hydroxyethylmercapto-5-nitrobenzoic acid of the formula

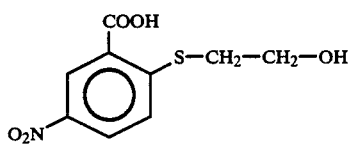

of melting point 189° to 191° C. and a purity (HPLC) of 99.1%.

Analysis: S: 13.2/13.0% (calculated 13.17%); N: 5.7/5.7% (calculated 5.76%); Cl: <0.3% (calculated 0.0%).

The procedure is repeated, except that potassium carbonate is replaced by equivalent amounts of potassium hydroxide or sodium hydroxide (in the form of 30 to 50% strength aqueous solutions) to give, if potassium hydroxide is used, a comparable result, and, if sodium hydroxide is used, an incomplete conversion, even if the reaction time is doubled, (yield: 104 parts of 2-hydroxyethylmercaptobenzoic acid of melting point 181° to 184° C., purity 96.2%).

EXAMPLES 2 TO 5

The procedure is repeated, except that in Example 1 the 6-chloro-3-nitrobenzoic acid is replaced by the isomeric chloronitrobenzoic acids listed in Table 1 to give the corresponding hydroxyethylmercaptonitrobenzoic acids in the yields and grades (melting point/purity) also listed in Table 1.

TABLE 1

| Ex. | Starting material | Target product Structure | Melting point | Yield | Purity (HPLC) |
|---|---|---|---|---|---|
| 2 | 5-Chloro-2-nitrobenzoic acid | 5-hydroxyethylmercapto-2-nitrobenzoic acid | 130–132° C. | 98.8% | 97.7% |
| 3 | 4-Chloro-3-nitrobenzoic acid | 4-hydroxyethylmercapto-3-nitrobenzoic acid | 179–182° C. | 97.1% | 98.4% |
| 4 | 3-Chloro-4-nitrobenzoic acid | 3-hydroxyethylmercapto-4-nitrobenzoic acid | 183–185° C. | 95.0% | 99.2% |
| 5 | 3-Chloro-2-nitrobenzoic acid | 3-hydroxyethylmercapto-2-nitrobenzoic acid | 138–140° C. | 93.8% | 98.0% |

Analyses of the target products confirm the structures given.

EXAMPLE 6

20.15 parts of 2-chloro-3-nitrobenzoic acid and 20.5 parts of potassium carbonate are successively added with stirring to 50 parts of N-methylpyrrolidone. The mixture is heated to 60° C., and 27.6 parts of 50% strength aqueous mercaptoethanol is then added dropwise over a period of 30 minutes.

After the mixture has been heated to 80° to 90° C., it is stirred until no more starting material can be detected in the thin-layer chromatogram (about 20 hours), water is then added in such an amount that the precipitated salts go into solution at 90° C., 1 part of activated carbon is added and the reaction mixture is clarified by filtering it through a preheated nutsche filter.

The clarified filtrate is brought to a pH of 1 with about 30 parts of 30% strength hydrochloric acid and cooled to 0° to 5° C. The reaction product which at first separates in the form of an oil slowly crystallizes completely upon stirring for several hours at 0° to 5° C., is filtered off with suction, washed free from chloride ions and solvents with icewater and is dried in vacuo at 60° C. This gives 20.0 parts of 2-hydroxethylmercapto-3-nitrobenzoic acid of the formula

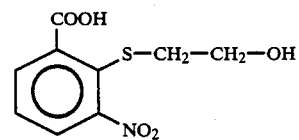

of melting point 91° to 93° C. and a purity (HPLC) of 99.4%.

The procedure is repeated, except that N-methylpyrrolidone is replaced by dimethylacetamide and the 30% strength hydrochloric acid is replaced by equivalent amounts of 20% strength sulfuric acid or phosphoric acid to give a comparable result.

EXAMPLE 7

9 parts by sodium tungstate dihydrate are added to a stirred suspension of 486 parts of 4-hydroxyethylmercapto-3-nitrobenzoic acid and 2,500 parts of water which had been brought to a pH of 1 with about 100 parts of glacial acetic acid, and the mixture is then heated to 75° C. 408 parts of 35% strength aqueous hydrogen peroxide are then added dropwise, at first slowly and without heating, and after the initial exothermic reaction has subsided, rapidly with additional heating at such a rate that the internal temperature can be maintained between 70° and 80° C., the mixture is then heated to 95° C. and is stirred for 4 to 5 hours at this temperature until the starting material and the sulfoxide formed as an intermediate are no longer visible on the thin-layer chromatogram. The mixture is then cooled to 0° to 5° C., stirred for 2 hours, and a colorless precipitate is isolated on a nutsche filter. The product is washed with icewater until neutral and dried in vacuo at 80° C. to give 525 parts of 4-hydroxyethyl-sulfonyl-3-nitrobenzoic acid of the formula

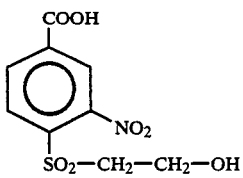

of melting point 191° to 193° C. and a purity (HPLC) of 98.8%.

Analysis: S: 11.6/11.5% (calculated 11.64%); N: 5.0/5.1% (calculated 5.09%).

The procedure is repeated, except that the sodium tungstate dihydrate is replaced by equivalent parts of tungsten trioxide to give an identical result.

The procedure is repeated, except that instead of glacial acetic acid a corresponding amount of a mineral acid (hydrochloric acid or sulfuric acid) is used for adjusting the pH to give the 4-hydroxyethylsulfonyl-3-nitrobenzoic acid in a comparable yield and grade.

EXAMPLES 8 TO 12

The procedure of Example 7 is repeated, except that the 4-hydroxyethylmercapto-3-nitrobenzoic acid is replaced by the isomeric starting materials listed in Table 2 to give the corresponding hydroxyethylsulfonylnitrobenzoic acids in the yields and grades (melting point/purity) also listed in Table 2.

drate are added to the resulting suspension and 350 parts of 30% strength aqueous hydrogen peroxide are then added dropwise over a period of 60 minutes at a temperature increasing from 60° C. to 90° C., and the mixture is stirred for 2 to 3 hours at 90° C. (monitored for complete conversion by thin-layer chromatography or HPLC).

The mixture is then cooled to 0° to 5° C., stirred for 2 hours, and the precipitated colorless crystals are filtered off with suction. Washing with icewater until the filtrate remains neutral and drying in vacuo at 90° C. gives 260 parts of 5-hydroxyethysulfonyl-2-nitrobenzoic acid of the formula

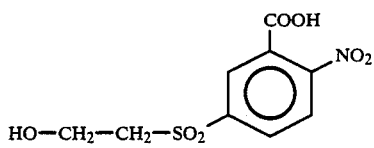

of melting point 165° to 167° C. and a purity (HPLC) of 97.9%.

The procedure is repeated, except that the 5-chloro-2-nitrobenzoic acid is replaced by 4-chloro-3-nitrobenzoic acid, to give 258 parts of 4-hydroxyethylsulfonyl-3-nitrobenzoic acid of melting point 190 to 192° C. and a purity of 97.0%.

EXAMPLE 14

40.3 parts of 3-chloro-4-nitrobenzoic acid and 44.6 parts of potassium carbonate are successively added with stirring to 100 parts of dimethylformamide. The mixture is heated to 40° to 45° C., and 75 parts of 40%

TABLE 2

| | | Target product | | |
|---|---|---|---|---|
| Ex. | Starting material | Structure | Melting point | Yield | Purity (HPLC) |
| 8 | 2-Hydroxyethylmercapto-5-nitrobenzoic acid | 2-hydroxyethyl-sulfonyl-5-nitrobenzoic acid | 172–175° C. | 95.8% | 97.9% |
| 9 | 3-Hydroxyethylmercapto-4-nitrobenzoic acid | 4-hydroxyethyl-sulfonyl-4-nitrobenzoic acid | 175–177° C. | 97.0% | 98.2% |
| 10 | 5-Hydroxyethylmercapto-2-nitrobenzoic acid | 3-hydroxyethyl-sulfonyl-2-nitrobenzoic acid | 166–168° C. | 96.6% | 98.5% |
| 11 | 3-Hydroxyethylmercapto-2-nitrobenzoic acid | 3-hydroxyethyl-sulfonyl-2-nitrobenzoic acid | 179–181° C. | 94.8% | 98.5% |
| 12 | 2-Hydroxyethylmercapto-3-nitrobenzoic acid | 2-hydroxyethyl-sulfonyl-3-nitrobenzoic acid | 183–186° C. | 91.5% | 96.9% |

Analyses of the target products confirm the structures given.

EXAMPLE 13

168 parts of potassium carbonate are slowly added to a stirred suspension of 201.5 parts of 5-chloro-2-nitrobenzoic acid and 250 parts of water over a period of about 40 minutes. The mixture is subsequently heated to 55° to 60° C., 109 parts of mercaptoethanol are added dropwise over a period of 2 hours, the mixture is stirred for about 3 hours at 70° to 75° C. until no more starting material can be detected by thin-layer chromatography, and is brought to a pH of 1 by running in about 180 parts of glacial acetic acid. 2 parts of sodium tungstate dihystrength aqueous mercaptoethanol are then added dropwise over a period of 45 minutes.

After the mixture has been heated to 90° to 95° C., it is stirred until no more starting material can be detected by thin-layer chromatography, then brought to a pH of 1.5 with about 65 parts of 30% strength hydrochloric acid and cooled to 50° to 60° C.

1 part of tungsten trioxide is added, 78.5 parts of 40% strength aqueous hydrogen peroxide is added dropwise to the stirred reaction mixture over a period of 90 minutes at a steady rate, during which the internal temperature may rise to 95° C., and stirring is continued until the oxidation is completed (about 5 hours, monitored by thin-layer chromatography or HPLC).

300 parts of water are then added, the mixture is cooled with stirring to 0° to 5° C., stirred for 90 minutes at 0° to 5° C., and the colorless precipitate is then filtered off with suction. The product is washed with icewater until neutral and dried at 80° C. in vacuo to give 51 parts of 3-hydroxyethylsulfonyl-4-nitrobenzoic acid of the formula

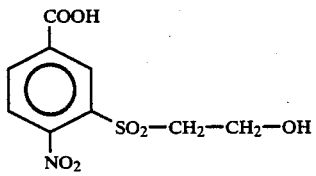

of melting point 176° to 177° C. and a purity (HPLC) of 99.3%.

The procedure is repeated, except that the 3-chloro-4-nitrobenzoic acid is replaced by 3-chloro-2-nitrobenzoic acid, to give 48 parts of 3-hydroxyethylsulfonyl-2-nitrobenzoic acid of melting point 178° to 181° C. and a purity (HPLC) of 98.8%.

EXAMPLE 15

75 parts of 3-hydroxyethylsulfonyl-2-nitrobenzoic acid are added at a steady rate over a period of 30 minutes with stirring to a mixture of 40 parts of iron powder and 200 parts of water heated to 80° to 85° C., and the reaction temperature of the mixture is maintained at 80° to 85° C. during the addition. After the addition is completed, the mixture is stirred for 30 minutes, brought to a pH of 8.5 with aqueous sodium carbonate solution and is clarified while hot by filtering off precipitated iron hydroxide. The filter residue is washed twice with a small amount of hot water. The combined filtrates are then acidified with 25 parts of glacial acetic acid, concentrated in vacuo to 150 parts by volume and subsequently cooled to 0° to 5° C. with stirring. The slightly brownish precipitate is isolated on a nutsche filter, washed with a small amount of icewater and dried at 60° C. in vacuo. This gives 78 parts of 3-hydroxyethylsulfonylanthranilic acid acetate of the formula

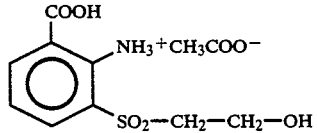

of melting point 286° to 289° C. and a purity by diazotization) of 99.5%.

Analysis: C: 43.2/43.3% (calculated 43.28%); H: 4.9/5.1% (calculated 4.92%); N: 4.6/ 4.6% (calculated 4.59%); S: 10.3/10.5% (calculated 10.49%).

EXAMPLE 16

The procedure of previous Example 15 is repeated, except that the 3-hydroxyethylsulfonyl-2-nitrobenzoic acid is replaced by 2-hydroxyethylsulfonyl-3-nitrobenzoic acid and, after the clarifying filtration to remove iron sludge, a pH of 6.5 to 7.0 is established to give 64 parts of 2-hydroxyethylsulfonyl-3-aminobenzoic acid of the formula

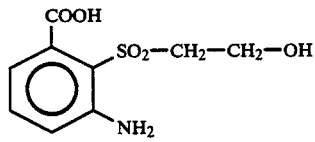

of melting point 75° to 77° C. and a purity (by diazotization) of 99.1%. Elemental analysis confirms the above structure.

EXAMPLE 17

1200 parts of water and 137.5 parts of 5-hydroxyethyl-sulfonyl-2-nitrobenzoic acid are initially introduced into a hydrogenation autoclave, and 10 parts of noble metal catalyst (5% of palladium on carbon) are added. The autoclave is sealed, and the gas space is freed from oxygen and nitrogen by flushing three times with nitrogen and then with hydrogen.

40 bar of hydrogen are then injected, and the mixture is heated to 90° C. The hydrogen pressure is maintained at 40 to 45 bar by constant additional injection of hydrogen. After 2 hours at 90° C., the absorption of hydrogen ceases. The autoclave contents are cleared of catalyst while hot by filtration through a pressure filter, and the filtrate is cooled to 0° to 5° C. with stirring. The precipitated colorless crystals are filtered off with suction, washed with a small amount of icewater and dried in vacuo at 60° C.

This gives 108 parts of 5-hydroxyethylsulfonylanthranilic acid of the formula

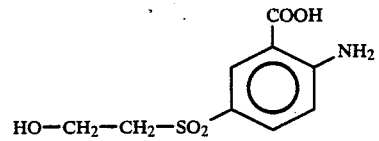

of melting point 164° to 167° C. having a purity (determined by diazotization) of 99.9%.

EXAMPLE 18

Example 17 is exactly repeated, except that instead of 1200 parts of water the aqueous mother liquor from Example 17 (about 1250 parts) and instead of fresh catalyst the Pd catalyst separated off from the hydrogenation mixture by clarifying filtration are used. This gives 120 parts of 5-hydroxyethylsulfonylanthranilic acid of melting point 164° to 167° C. and a purity (diazotization) of 99.8%.

EXAMPLES 19 TO 27

The procedures of Examples 17 and 18 are repeated, except that in each case 137.5 parts of 5-hydroxyethyl-sulfonyl-2-nitrobenzoic acid and also the aqueous mother liquor and the Pd catalyst of the previous batch are used, to give in each case about 122 parts of 5-hydroxyethylsulfonylanthranilic acid of melting point 164° to 166° C. and a purity (diazotization) of >99%, that is, mother liquor and catalyst can each be used at least 10 times without deterioration of the product or decrease in yield.

EXAMPLE 28

The procedure of Example 17 is repeated, except that the palladium catalyst is replaced by a commercially available platinum or nickel supported catalyst, to give the 5-hydroxyethylsulfonylanthranilic acid in comparable yield and grade.

EXAMPLES 29 TO 31

The procedures of the previous Examples 16 or 17 to 27 are repeated, except that the hydroxyethylsulfonylnitrobenzoic acids used in these examples are replaced by the starting materials listed in Table 3, to give the corresponding hydroxyethylsulfonylaminobenzoic acids in the yields and grades (melting point/purity by diazotization) also listed in Table 3.

TABLE 3

| Ex. | Starting material | Target product Structure | Melting point | Yield | Purity (diaz.) |
|---|---|---|---|---|---|
| 29 | 4-Hydroxyethylsulfonyl-3-nitrobenzoic acid | 4-hydroxyethyl-sulfonyl-3-aminobenzoic acid | 183–186° C. | 97.5% | 99.2% |
| 30 | 2-Hydroxyethylsulfonyl-5-nitrobenzoic acid | 2-hydroxyethyl-sulfonyl-5-aminobenzoic acid | 47–50° C. | 91.8% | 99.4% |
| 31 | 3-Hydroxyethylsulfonyl-4-nitrobenzoic acid | 3-hydroxyethyl-sulfonyl-4-aminobenzoic acid | 220–223° C. | 97.1% | 99.4% |

I claim:
1. A compound of the formula

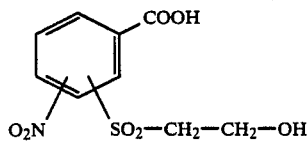

in which the nitro and hydroxyethylsulfonyl group are in the ortho- or para-position relative to one another.

* * * * *